United States Patent [19]

Spitzer et al.

[11] Patent Number: 5,092,343
[45] Date of Patent: Mar. 3, 1992

[54] WAVEFORM ANALYSIS APPARATUS AND METHOD USING NEURAL NETWORK TECHNIQUES

[75] Inventors: Robert Spitzer, W. Bloomfield; Mohamad Hassoun, Dearborn, both of Mich.

[73] Assignee: Wayne State University, Detroit, Mich.

[21] Appl. No.: 438,581

[22] Filed: Nov. 17, 1989

Related U.S. Application Data

[63] Continuation-in-part of Ser. No. 157,324, Feb. 17, 1988, abandoned.

[51] Int. Cl.⁵ .............................................. A61B 5/05
[52] U.S. Cl. .............................. 128/733; 364/413.05
[58] Field of Search .............. 128/696, 702, 731, 733; 364/413.02, 413.05, 413.06

[56] References Cited

U.S. PATENT DOCUMENTS

| | | | |
|---|---|---|---|
| 4,603,703 | 8/1986 | McGill et al. | 128/733 |
| 4,611,284 | 9/1986 | McGill et al. | 128/733 |
| 4,665,485 | 5/1987 | Lundy et al. | 128/702 |
| 4,742,458 | 5/1988 | Nathans et al. | 128/702 |

Primary Examiner—William E. Kamm
Attorney, Agent, or Firm—Reising, Ethington, Barnard, Perry & Milton

[57] ABSTRACT

A waveform analysis assembly (10) includes a sensor (12) for detecting physiological electrical and mechanical signals produced by the body. An extraction neural network (22, 22') will learn a repetitive waveform of the electrical signal, store the waveform in memory (18), extract the waveform from the electrical signal, store the location times of occurrences of the waveform, and subtract the waveform from the electrical signal. Each significantly different waveform in the electrical signal is learned and extracted. A single or multilayer layer neural network (22, 22') accomplishes the learning and extraction with either multiple passes over the electrical signal or accomplishes the learning and extraction of all waveforms in a single pass over the electrical signal. A reducer (20) receives the stored waveforms and times and reduces them into features characterizing the waveforms. A classifier neural network (36) analyzes the features by classifying them through nonliner mapping techniques within the network representing diseased states and produces results of diseased states based on learned features of the normal and patient groups.

33 Claims, 10 Drawing Sheets

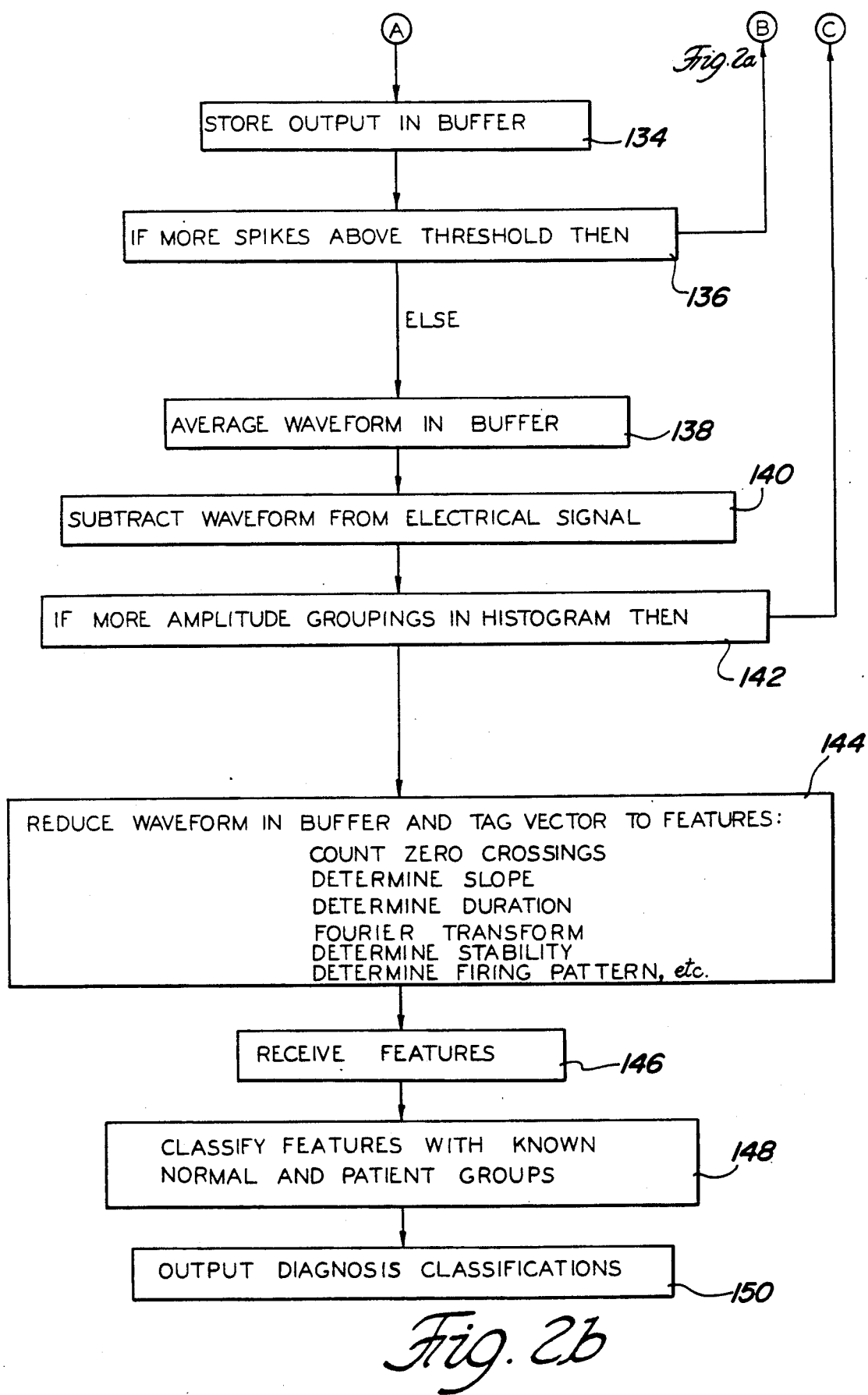

WAVEFORM ANALYSIS APPARATUS AND METHOD USING NEURAL NETWORK TECHNIQUES

RELATED APPLICATIONS

The application is a continuation-in-part of U.S. Ser. No. 157,324, filed Feb. 17, 1988, now abandoned.

TECHNICAL FIELD

The invention relates to analyzing unknown and repetitive waveforms of electrical signals produced by the body for determining diseased states.

BACKGROUND OF THE INVENTION

Under various circumstances, it is desirable to analyze an electrical signal comprising a repetitive waveform. In order to analyze the waveform, the waveform must be identified and extracted. One example of extensive efforts to analyze repetitive waveforms in an electrical signal has been in the field of electromyography.

Electromyography (EMG) is an important tool in the diagnosis of diseases of the peripheral nervous system. An EMG signal is recorded from a needle inserted into a specified muscle, and represents the electrical discharge of groups of muscle fibers. Abnormality is estimated by observing the potentials on an oscilloscope screen. Reliability of the technique for the diagnosis of diseases of the peripheral nervous system have been seriously limited by a lack of a method to accurately and quickly quantity features of the EMG. Additionally, extension of the use of the EMG to diagnosis of disorders of the central nervous system has been limited by an ability to accurately measure pattern information by visual estimation. In visual diagnosis, the physician sees potentials that flicker across the oscilloscope screen at 10 to 30 Hz, and listens to the sound on a loud speaker. The results are also highly dependent on the training of the individual performing the examination and subject to bias. This accounts for limitations on the reproducibility and reliability of the test in diagnosis of diseases of the peripheral nervous system. Another significant limitation is the inability of the observer to quantify certain perimeters such as firing rate and pattern, and relationships between firing patterns and recruitment of units. While attempts have been made by more experienced physicians and researchers to extend EMG to the diagnosis of diseases of the central nervous system, an ability to accurately measure appropriate perimeters have prevented realization of this goal.

Previous attempts to apply computer analysis to the EMG signal have been marginally successful because the signal is extremely variable and complex. Recently, new methods based on modelling of processing (computation) by biologic neurons have demonstrated better capabilities than traditional algorithms for analyzing complex signals such as images or voice signals.

A first method for a motor unit quantitation was developed by Buchthal. "Action Potential Parameters in Normal Muscle and Their Dependence on Physical Variables", F. Buchthal, C. Gold, P. Rosenfalck. Acta Physiol Scand, 1954a (32) 200. His method involves the recording of randomly collected motor units on photographic film or paper. The motor units are visually inspected, and duration, amplitude and phases measured and tabulated. After 20 or more units are measured, resulting mean values are compared with normative data collected by Buchthal. This method is extremely time consuming, taking up to an hour for a single muscle. Since most clinical studies involve examining up to a dozen muscles or more, this method is not practical except in a research setting. Again, it is subject to significant bias by the individual selecting and measuring the units.

Several computer assisted methods of MUP quantization have been developed initially as research tools. The computer programs have generally been developed on laboratory mini computers, and after they have been published they have been made available as software packages.

One of the most significant efforts has been by Dorfman and McGill. "Automated Decomposition of the Clinical Electromyogram", K. C. McGill, K. L. Cummins, L. J. Dorfman. IEEE Trans. Biomed. Eng., 32 (7): 470-477, July 1985. This program is called ADEMG (Automated Decomposition of the EMG). The program records the interference pattern at threshold, 10% or 30% of maximal effort. It then filters and differentiates the signal to locate the motor unit spikes. Motor units are isolated and compared by a template matching scheme. Recurrences of the same unit are aligned in the Fourier domain, and averaged. Superimpositions are resolved whenever possible during matching. A final average is then reprocessed to remove adjacent or overlapping units that may be degrading the average. Duration is computed automatically. Firing rate is analyzed, but is used merely to locate missing occurrences of motor units. No further processing is performed. In general, this method identifies waveforms by two characteristics: firing pattern and template matching. One waveform is subtracted from another, and if the difference is close, it is considered the same waveform. The waveforms are then averaged. This method may erroneously resolve polyphasic motor units into discrete components, thus failing in disease states where motor unit phases are increased. While the program tracks slowly varying wave shapes, it has trouble detecting repeated occurrences of the same when that unit is unstable in configuration, as is the case in several disease states. Under these circumstances, ADEMG may erroneously detect the slightly different occurrences as distinct motor units. The ADEMG only averages waveforms to produce a template; there is no training or learning. Furthermore, the algorithm does not classify the waveform.

An additional signal processing method has been by Gevins. "Igorance-based Neural-Network Signal Processing in Brain Research", Alan S. Gevins and Nelson H. Morgan, June 1987. The method outlined in the paper looks at the application of neural-network classifier-directed methods to known neurological waveform detection. The methods include application to contaminant detection for replacement of ad-hoc detectors, and waveform detection for evoked potential estimation.

In the application of contaminants, expert knowledge of contaminant types is represented by training data which have been hand-marked, which is used to train a neural network to distinguish clean from contaminated data. Several neural networks are used, each trained to detect a different type of contaminant. However, the network is manually trained by known patterns and just detects the known patterns occurring in the raw data. The network of this method is incapable of receiving a large number of features and classifying the input on best match; the method only accepts raw data and not features. Furthermore, the method does not disclose any type of initial waveform identification. In the evoked potential estimation, assumptions about the signal and noise properties are necessary based on potential. This method requires preconceived assumptions of the input signal in order to operate.

The prior art requires prior information regarding the data signal in order to process the waveforms. Problems arise when the waveform does not match any of the original assumptions, or there is a superimposition of waveforms. The prior art cannot learn new and unknown waveforms and cannot classify unknown patterns or waveforms.

Most of the prior art utilizes one of the following methods in order to classify the waveform: rule base system, pattern match, or look up table. None of the prior art uses a dynamic architecture which maps the features for classifying the diagnosis.

The following prior art has made attempts to either identify a waveform or classify the waveform, however, none of the prior art is capable of learning an unknown waveform or classifying features by network transformation.

U.S. Pat. No. 4,453,551 issued June 12, 1984 to Anderson et al discloses a pattern recognition assembly for ECG signals for detecting fibrillation. The signals are digitized, stored, and subjected to an AGC routine. Thereafter, samples are subjected to a series of tests to detect an abnormal physiological condition. Various tests which are preformed include determining the amount of zero crossings, ratio of energies contained in the ECG trace, and analyzing the slopes of the ECG signal. The Anderson patent discloses extracting known waveforms and measuring features. The Anderson patent extracts features without looking at the waveform. Anderson does not attempt to identify unknown waveforms but only identifies the presence of known waveforms shapes. Furthermore, the waveform is not extracted.

U.S. Pat. No. 3,858,034, issued Dec. 31, 1974 to Anderson discloses a computer system for detecting QRS complexes of known configurations. The system extracts from the complexes various descriptive features. The system will not detect unknown waveforms nor analyze the entire waveform for classification thereof.

U.S. Pat. No. 3,606,882, issued Sept. 21, 1971 to Zenmon et al discloses a system for diagnosing heart disease which separates the p Waves or the QRS wave from a waveform or cardiac potential. Such a system is representative of typical detectors used in EKG signals which is merely looking for a known waveform and identifies the presence or absence of the waveform.

U.S. Pat. No. 3,587,562, issued June 28, 1971 to Williams discloses a physiological monitoring system which receives physiological signals comprising both respiration and cardiac action. Williams discloses a standard method of recording cardiac and pulmonary signals which is used in any type of physiological system.

U.S. Pat. No. 4,338,950, issued July 13, 1982 in the name of Barlow, Jr. et al discloses a system for sensing and measuring heart beats without the effect of body motion. The Barlow system is a simple detector which identifies the presence of pulse waves from the heart beat. Once a waveform is identified based on a known waveform, the number of waveforms are merely counted. There is no learning nor diagnosis.

U.S. Pat. No. 4,754,762, issued July 5, 1988 to Stuchl discloses an EKG monitoring system which receives the heart muscle signal and isolates the QRS components. The Stuchl reference discloses a typical EKG system wherein the waveform is decomposed and the entire waveform itself is not learned. The system merely detects the presence or absence of a known waveform or it looks for a specific feature.

U.S. Pat. No. 4,770,184, issued Sept. 13, 1988 to Greene, Jr. et al discloses an ultrasonic doppler diagnostic system which utilizes pattern recognition. The Greene discloses a standard fast fourier transform device to obtain a spectrum. The Greene utilizes a known pattern and attempts to diagnose abnormalities on the basis of doppler. Prior knowledge of stored set of known patterns are utilized and the closest match within the data base is used for recognition thereof.

U.S. Pat. No. 4,566,464, issued Jan. 28, 1986 to Piccone et al discloses an epilepsy monitor apparatus for analyzing EEG patterns and an unobtrusive external warning unit to inform the patient of seizure onset. The Piccone reference merely discloses a detector which is designed to recognized the presence or absence of known waveforms. There is no learning nor extraction nor diagnosis. The signal is recorded which is known to be abnormal or epileptic. Then the device differentiates between two types in order to warn.

U.S. Pat. No. 3,902,476, issued Sept. 2, 1975 to Chaumet discloses an apparatus for heart beat rate monitoring. An electrocardiogram signal and the derivative in relation to time of such signals are applied as input with the maximum amplitude of each of the signals stored, and the maximum amplitude of the interference signals are stored so that the crest-to-crest amplitude of the electrocardiogram signal and the crest-to-crest amplitude of the derivative in relation to time of such signals are obtained. This device does not identify or decompose waveforms nor does it take a waveform and extract the waveform from the original signal. The sensed signal must match exactly for identification thereof.

All of the above noted patents are generally detectors which detect either features of a waveform or known waveforms. None of the prior art discloses learning an unknown waveform and classifying the waveform by nonlinear dynamic architecture.

SUMMARY OF THE INVENTION

The invention is the method of discriminating physiological signals and a wave analysis assembly for discriminating physiological signals produced within the body and for producing output indicative of disease characteristics. The assembly includes sensing means for sampling a physiological signal produced within the body and for producing an electrical signal. The assembly also includes control means for identifying the location of individual waveforms occurring about a peak within the electrical signal and producing a learning set comprised of the individual waveforms of one repetitive waveform, extraction network means for receiving the learning set and for learning the repetitive waveform within the electrical signal by mapping the individual waveforms of the learning set to produce a learned waveform and for extracting the learned waveform from the electrical signal. Output means establishes a diagnosis and outputs information regarding the disease diagnosis based on the extracted waveform.

The assembly also includes classifier means containing information comprising learned features and combinations thereof associated with disease states for mapping the features to the information to produce an output representative of diseased states by the best match based on a mapping transformation of the features with the information. The invention also applies to other applications which produce electrical signals having a repetitive waveform.

The assembly is advantageous over the prior art in that the assembly will learn a repetitive waveform and is therefore able to handle superimpositions, polyphasic waveforms, and nontemplated waveforms. Additionally, the assembly also will produce the best match of diseased state without requiring an exact match of all features. In other words, the assembly may receive an unknown data signal and learn a repetitive waveform from that signal without any pre-conceived information regarding the waveform, and extract the learned waveform from the data signal.

BRIEF DESCRIPTION OF THE DRAWINGS

Other advantages of the present invention will be readily appreciated as the same becomes better understood by reference to the following detailed description when considered in connection with the accompanying drawings wherein.

DESCRIPTION OF THE PREFERRED EMBODIMENT

Figure 1:
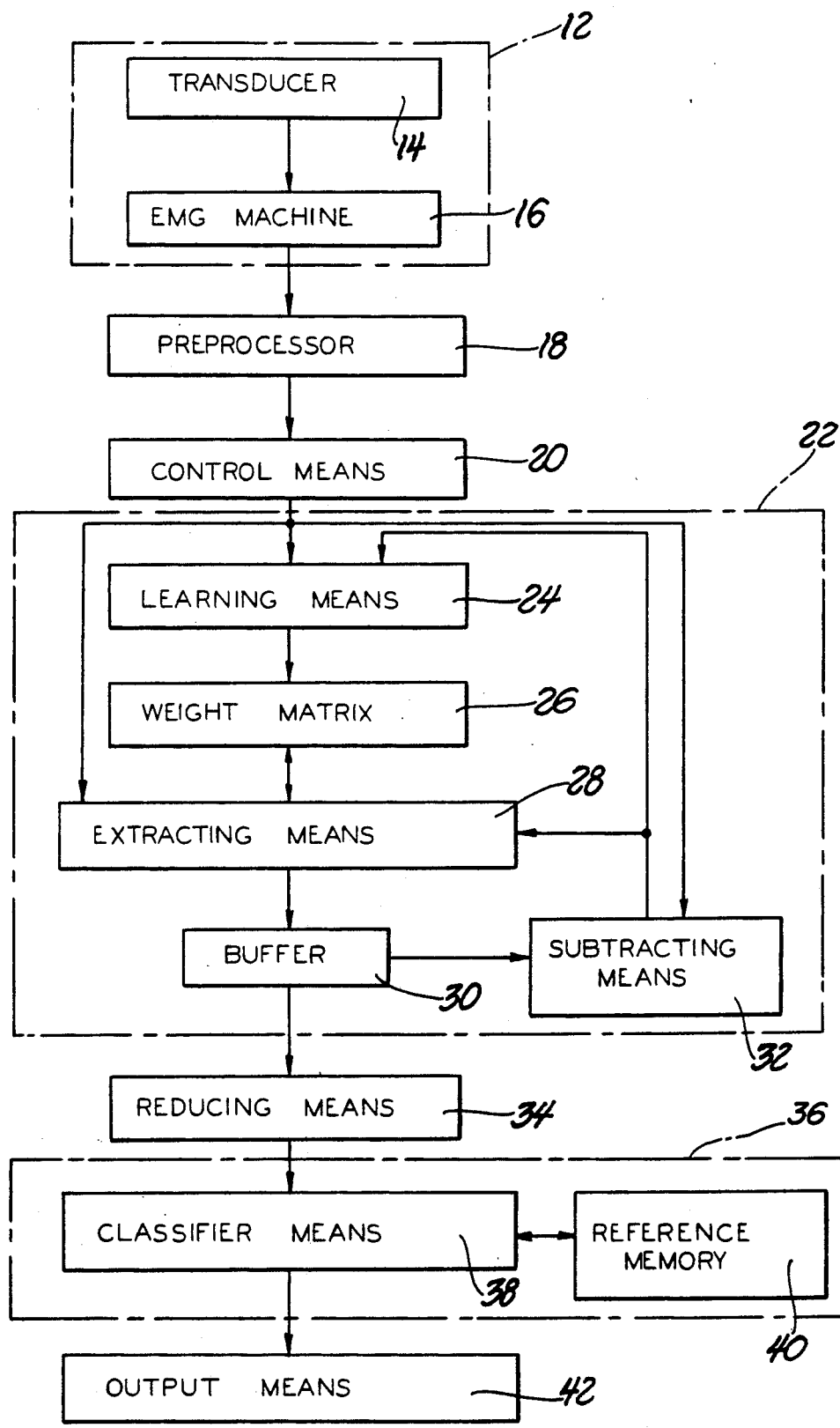
FIG. 1 is a block diagram of the subject invention.

A wave analysis assembly is generally shown at 10 in FIG. 1 and implements the flow chart in FIG. 2. The wave analysis assembly and method may applied to any physiological electrical or mechanical signals sensed from internal activity, such as electromyography (EMG), electroencephylogram (EEG), and electrocardiogram (EKG), etc. The preferred embodiment of the subject invention is directed toward diagnosing neuromuscular disorders and will be defined in this application, but the apparatus and method may be applied to detecting and analyzing physiologic waveforms from any source. Electromyography is a technique for diagnosing neuromuscular disorders by analyzing the electrical signal recorded from a contracting muscle using a needle electrode 12.

By way of background, the electrical signal recorded as an electromyogram (EMG), is made of trains of discrete waves called motor unit potentials. The motor unit potentials (MUP) may be defined as the electrical potential within a muscle produced by the simultaneous discharge of all the muscle fibers connected to a single motor neuron. The lower motor neuron is the neuron in the spinal cord whose axon directly connects to a group of muscle fibers in a specific muscle. Each discharge of this neuron directly discharges the muscle fibers, causing them to contract. The firing of this neuron is under the control of the other neurons in the central nervous system, including the upper motor neurons. Because of the intimate relationship with the peripheral nerve and muscle fibers, this neuron can properly be considered functionally part of the peripheral nervous system, even though it is physically within the central nervous system.

A neuron's major property is its ability to produce a frequency output in response to the processing of multiple inputs from other neurons. The same term is used to indicate a mathematically modeled neuron which is the basic element of a neural network.

A neural network, also termed parallel distributed processing, perception, associative memory, etc., is a simulated or physically constructed array of modeled neurons. The array has input connections, interconnections between neurons, and output connections, generally called the synaptic weight matrix. The simplest arrays are linear, but more complex architectures are under investigation. The processing accomplished by the array occurs in parallel, and is dependent on both the physical architecture of interconnection, and the strengths of interconnection or the elements. The graphs illustrated in FIGS. 3-6 and 10-11 are simulated to represent actual EMG signals. The X axis is time and the Y axis is magnitude. With respect to the EMG signals, the time is in milliseconds and the magnitude is in microvolts.

Figure 2A:
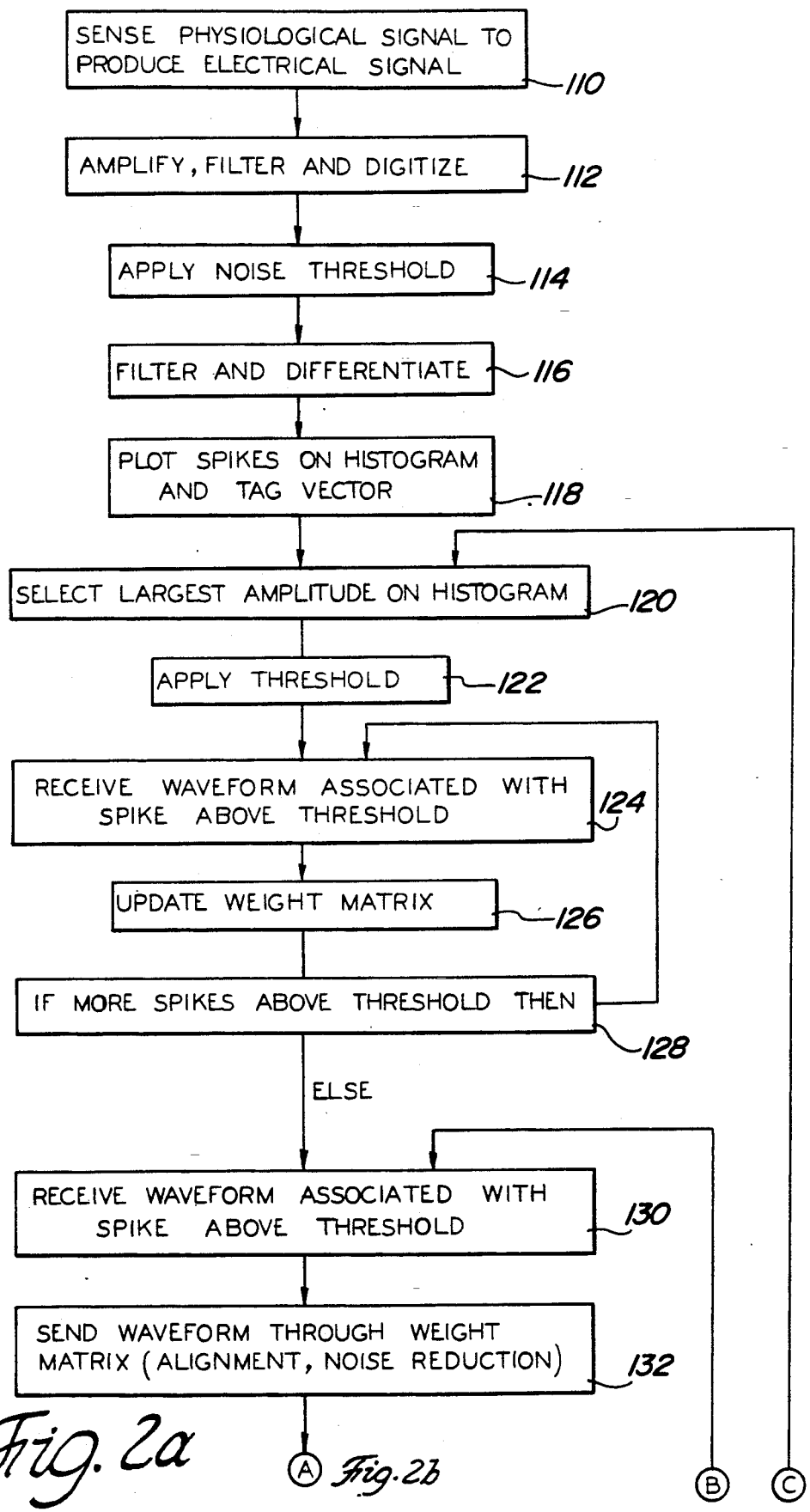
FIGS. 2a and b are the flow chart defining the block diagram of FIG. 1.

As indicated in FIGS. 1 and 2a-2b, the assembly 10 includes the general steps of sampling the physiological signal 12 (flowchart step 110), preprocessing 18 (flowchart steps ) the signal, learning and extracting 22 (flowchart steps 124-142) a waveform, reducing 34 (flowchart step 144) the waveform to features, and classifying 36 (flowchart steps 146-150) the feature to produce a diagnostic information or interpretable output. A user interactive system will allow review of the raw electrical signal and extracted motor units to verify accurate performance. Each step will be subsequently described in detail.

FIG. 1 illustrates the block diagram of the subject invention, and FIGS. 2a-2b illustrates the associated flow chart for implementing the means of FIG. 1.

Figure 3:
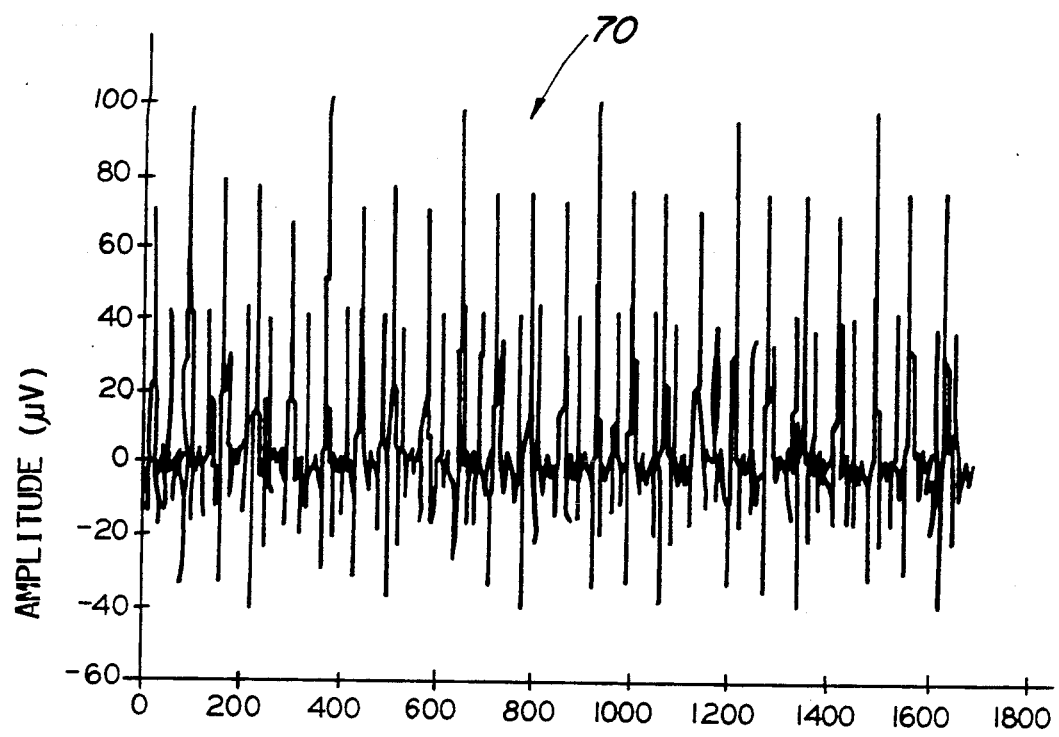
FIG. 3 illustrates a simulated electromyogram containing two motor units and noise.

The assembly 10 includes sensing means 12 for sampling the physiological signal produced within the body and for producing an electrical or original signal as indicated in step 110. The sampling means 12 may include any type of transducer for converting the sensed data into an electrical signal. The sensing means 12 includes a concentric needle electrode or monopolar needle electrode 14. The sensing means 12 also includes a standard EMG machine 16 which amplifies and filters the signal from the needle and an analog to digital converter producing a digitized electrical signal for processing. FIG. 3 illustrates a simulated EMG signal as would be sensed and which includes the repetitive occurrence of two motor units. Preferably, ten seconds of EMG signal will be sampled at each needle 14 insertion site. Since typical motor unit firing rates are approximately 10 Hz, it is estimated that 100 occurrences of each unit will be obtained in the sampled sweep. The EMG will be analyzed at minimal or threshold effort and at 10% and 30% of maximal effort. Experience has indicated that up to five or six units can be analyzed at each site, but the invention is not limited to this number.

The assembly 10 also includes preprocessing means 18, which is optional, for filtering and differentiating the electrical signal to isolate spikes associated with the waveforms as indicated in step 112. If the "turns list" method is used, as subsequently described, the filtering and differentiating is not required. The preprocessing 18 may incorporate the method as set out in the McGill reference comprising filtering and identification of the motor unit spike locations. The noise level of the electrical signal may be determined using the algorithm developed by McGill and Dorfman, this establishes a threshold below which peaks in the signal are not considered to represent candidate motor units as indicated in step 114. A standard upper filter setting of 10 KHz and a sample rate of 20KHz is preferably used. Initial work suggests Fourier interpolation will not be necessary, but this can be added later if needed. The spikes generally indicate the location of a motor unit occurrence, and its associated waveform. Peaks in the waveform are detected by a simple sign-change algorithm that approximates a differentiator and zero crossing detector.

The assembly 10 includes control means 20 for identifying spikes associated with individual waveforms and their respective locations. The control means 20 may be simply implemented through software. The spikes are sorted by amplitude, and an amplitude histogram is made and used to isolate the groups of amplitude as indicated in steps 116-122. The amplitude of every spike is taken to make the histogram. A histogram is a plot of the amplitude versus the number of occurrences. A tag vector associated with all the detected peaks is also made. The tag vector indicates the time location of the peak occurrences. The spikes for a single motor unit tend to cluster around a single amplitude. It is assumed for the assembly 10 that each peak or grouping of potential represents one motor unit. The histogram has peaks and troughs. A threshold is selected for each trough in the amplitude histogram. Processing begins with the group of spikes associated with the amplitudes lying to the right of the first trough in the histogram. These spikes are identified by simple threshold detection, with the trough value determined from the histogram determining this threshold. The tag vector locations associated with these spikes are likely to identify the largest motor unit potential waveform in the data.

The assembly 10 includes extracting network means 22 for receiving the electrical signal and for learning the repetitive waveform components within the electrical signal and for extracting the learned waveform. The extracting network means 22 is a neural network.

The extracting network means 22 includes buffer means 30 for storing the extracted waveform and associated times of occurrence of the waveform within the electrical signal. Peaks less than a specified magnitude, for example 100uV, are assumed to be noise and are not processed. Therefore, only spikes and associated waveforms above the threshold will be learned and extracted.

The first step of the extracting neural network 22 is the learning step implemented by learning means 24. Each waveform associated with an isolated spike will be analyzed. The data centered at each detected spike above the highest threshold is fed into the network 22 from the control means 20. The neural network 22 will make a pass over the electrical signal and learn the appearance of each motor unit at each spike location in the histogram grouping. The learning means 24 can learn any number of linked waveforms, polyphasic waveforms, or complex waveforms but will reject superimpositions. An entire waveform, which may be 256 sample points, is received in parallel. Each occurrence of a waveform will be taken and fed into the neural network 22. Each motor unit identified in this manner is processed by the extracting neural network 22 separately, in reverse order with respect to amplitude. Therefore, the motor unit associated with the largest amplitude will be processed first. This is illustrated in steps 124-128.

The first step of the extraction network 22, which is performed by the learning means 24, is to make a first pass over the signal and synthesize a weight matrix for a motor unit. The extraction network 22 is controlled by the control means 20 as to which waveform to learn an respective locations of the spike associated therewith, by applying the threshold. It is to be understood, that the extraction network 22 may implement the functions of the control means 20, thus eliminating the necessity of the control means 20. The weight matrix 26 is the configuration used to describe the form of storage and processing of a motor unit waveform within a neural network 22, as is known in the art. The learning means 24 receives the sampled data points of a motor unit waveform and stores the information in the weight matrix 26 in a representative distributed fashion called the synaptic weight measurement. The array of inputs or sampled points surrounding a peak or spike are fed into the first neural network 22. The system generally looks at a 10-20 msec duration or window of a motor unit, but may obtain a maximum window of generally 100 msec, but this window may vary. Single motor units with waveforms greater than 100 msec would be obvious to a diagnosing physician of a disease. If there are two motor units within a window, the neural network 22 initially assumes a complex waveform. If this is in fact not a complex waveform but a superimposition, it is unlikely to occur often within the complete 10 second sampling period, and will therefore be "forgotten". Since a single motor unit is consecutively detected approximately 100 times within the 10 msec sampling period and learned, a few wrong or odd waves will not effect the learned waveform. If the two waves or superimposition do always occur, the learning means 24 of the neural network 22 can detect and learn this waveform. Therefore, the learning means 24 will search the electrical signal for each peak or waveform associated with the specific amplitude grouping of the histogram, and will learn the waveform by adjusting the waveform by a factor of 1/K upon detection of each spike of the specific amplitude. The learning means 24 will look at K waveforms, approximately 100 waveforms but which may vary, and learn the waveform by updating the learned waveform in an averaging fashion. In other words, the learning means 24 of the neural network 22 receives the first waveform approximately associated with the amplitude grouping from the histogram. The learning means 24 stores this waveform in the weight matrix 26 and then detects another waveform of similar amplitude and "averages" them by a factor of 1/k. This process is continued until the first pass is completed and all waveforms above the threshold are learned. Upon completion of this learning pass, an idealized representation of the motor unit potential waveform resides in the network's weight matrix 26 in a distributed fashion. Therefore, any repetitive waveform shape may be learned and stored in the weight matrix 26.

Figure 4:
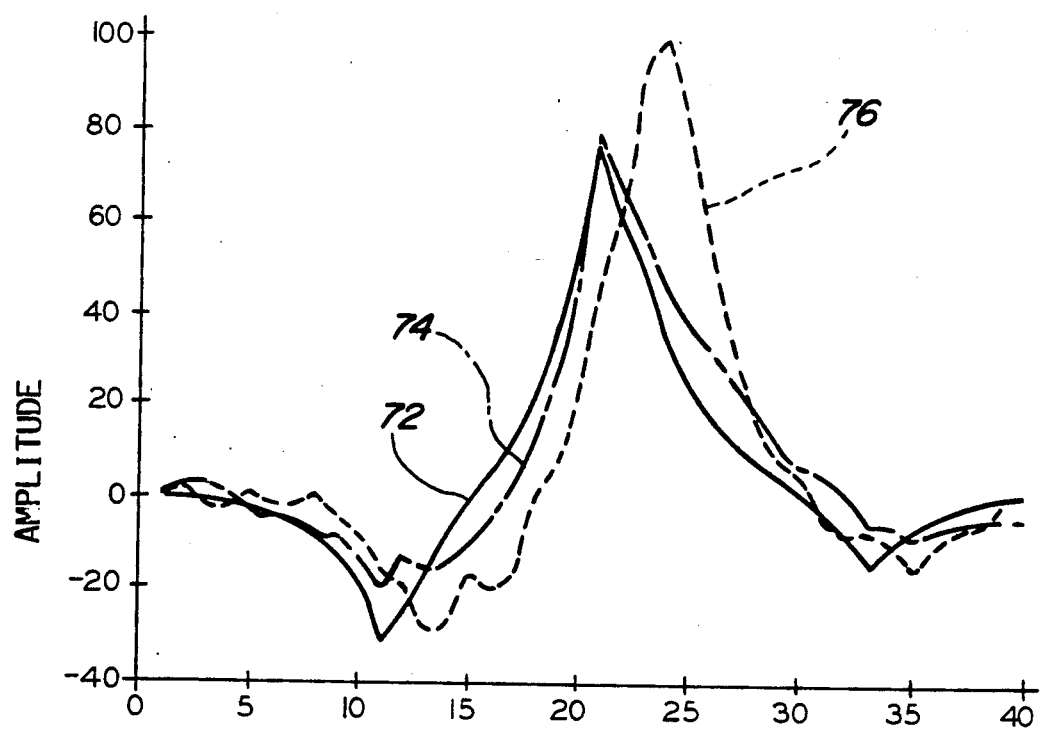
FIG. 4 illustrates a learned motor unit and a sampled motor unit for extraction.
Figure 6:
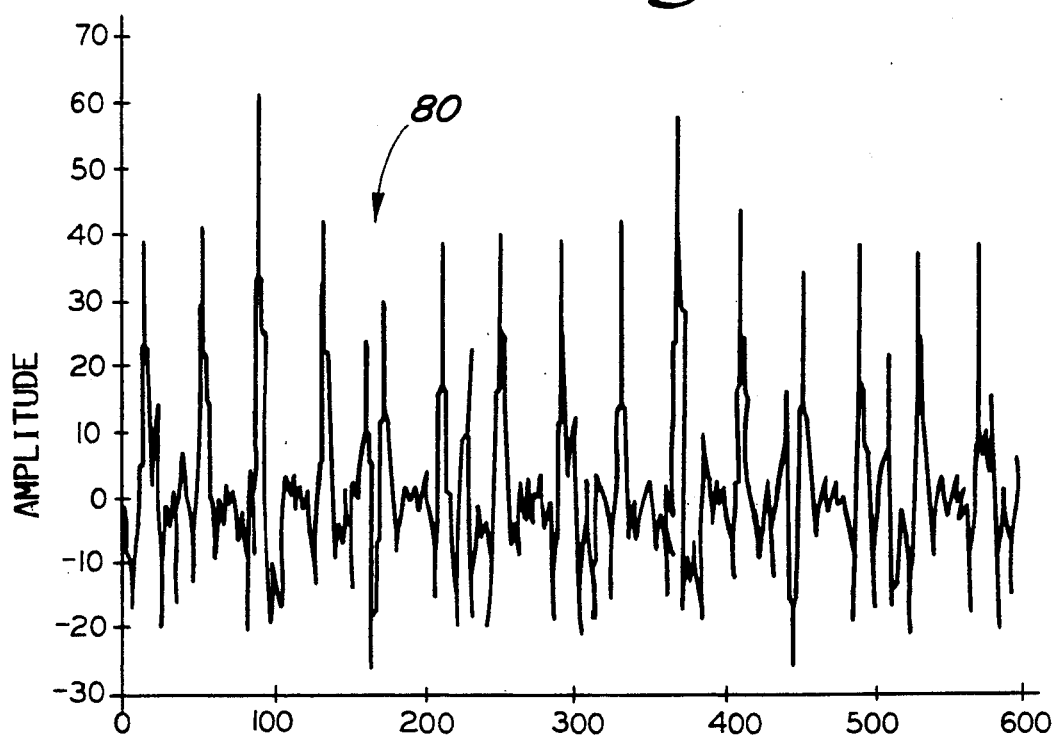
FIG. 6 illustrates the electrical signal after subtraction of the first MU.

During the second pass of the electrical signal by the neural network 22, there is no further learning. The second pass is an extraction pass which implemented by extracting means 28 within the neural network means 22 indicated in steps 130-142. The weight matrix 26 is not adjusted. The idealized representation of the motor unit waveform is now retrieved from the weight matrix 26 of the network 22. The same occurrences centered at the same spikes as during the learning pass are used as input. As each candidate occurrence of the motor unit is presented, the extracting means 28 responds with an output that represents an extraction of the underlying motor unit potential and is stored in a summing buffer 30. This extracted waveform retrieved by the extracting means 28 is aligned in the least-squares sense. The extraction pass includes aligning, and removing noise and superimpositions as indicated in FIG. 4. If the amplitude or waveform shape is very different from the learned waveform, this will be indicated as wrong and ignored. Slight variations will not throw off the extracting means 28, and it will look for these occurrences. Therefore, the original electrical signal is received and compared to the learned waveform representation in the weight matrix 26, and the output which is aligned and noise removed is sent to a summing buffer 30 for averaging. A time table or tag vector in the buffer 30 is produced indicating the time of each occurrence of the motor unit. The firing pattern associated with this time table of a single motor unit is used to investigate possible intermediate occurrences of the motor unit that were missed by the amplitude criterion. Spikes in the vicinity of such missing locations are evaluated by the neural network 22 to determine if they represent the unit being analyzed. The firing pattern, thus extracted, represents an important feature of the signal, and is used for classification. When there is a match of the waveform in the electrical signal, the time occurrence is stored and the waveform is extracted from the electrical signal to the summing buffer 30. The differences are extracted and superimpositions that do not match are thrown out of the electrical signal output of the second pass. In other words, for each input, the resultant network output is summed in the buffer 30 and the final result averaged. Automatic alignment is accomplished during the extraction pass. FIG. 6 indicates a resulting signal after the extraction of a motor unit from the original signal of FIG. 3. The process of learning and extracting is repeated for each motor unit and associated waveform.

After one motor unit is learned, the third step of the network 22 is to subtract the motor unit from the electrical signal at each tag vector location before processing another motor unit which is implemented by subtracting means 32. Since the neural network learns the entire shape of the waveform within its window, including all adjoining peaks that belong to the same motor unit, this step removes all associated peaks. This includes all of the peaks associated with polyphasic or satellite waveforms. Complex waveforms are not processed incorrectly as separate motor unit potentials.

After the first and greatest amplitude grouping from the histogram is analyzed by this process and subtracted form the electrical signal, the next greatest amplitude grouping is analyzed which is presumed to be associated with a another motor unit. This process continues for each amplitude grouping of the histogram, and the learned and extracted waveform of each associated motor unit is stored in a separate buffer 30. It is to be noted that for subsequent motor units, the resultant signal outputted from the subtracting means 32 will be used as the electrical signal for the next learning and extraction. When another motor unit is to be processed, the previous already processed motor units have been subtracted from the electrical signal and are therefore not included in the processed signal, as indicated in FIG. 6.

In other words, the neural network 22 detects and learns and then extracts one waveform, and then will repeat to find another waveform based on the next largest amplitude of the histogram. During the subtraction step, the learned waveform is aligned on the largest peak of the sampled waveform. The system can analyze polyphasic and subtract slight variations. Peaks less than 100uV are assumed to be noise and are not processed.

In other words, the neural network 22 is a dynamic network which learns and decomposes waveforms. The network does not simply utilize a look-up table, pattern matching nor rule based scheme. During the learning, the neural network 22 develops an idealized representation of the waveform which may never occur as such in the raw data or original electrical signal. The idealized representation is stored in the neural network 22 in a distributed manner in the weight matrix. The neural network's 22 nonlinear mapping capabilities detect a match of an unknown waveform to the presently learned waveforms, or determines it as a new waveform. The learning algorithm is accomplished by taking the error signal and modifying the synaptic weights to reduce the error. The error signal is obtained by taking the raw input waveform, sending it through the network 22 to obtain an output network signal which is the transformation of the input signal by the synaptic weights of what the network 22 believes the waveform looks like. The raw input waveform is compared to the transformed output waveform to produce the error signal. The error signal is used to partially update the weight matrix to gradually converge the network 22 to an idealized waveform. The gradual updating of the synaptic weights by using corrupt inputs is the pseudo-unsupervised learning of the network 22. The learning does not require or utilize the identification of features of the waveform. When the learning is complete, the information of one or a plurality of waveform is scattered throughout the weights in the architecture or network 22. The network 22 is then capable of detecting the presence of a waveform in the original electrical signal The network 22 has stored by the weight matrix an idealized waveform; the actual data may not look like the idealized waveform. In order to obtain the idealized waveform stored in the network 22, the raw data is input into the network 22 and the network 22 converges by continuously feeding back its output signal into the network 22 until the waveform reaches a stable state. The network 22 may have a plurality of idealized waveforms stored therein, therefore, at least one similar waveform must be input to the network 22 for convergence to an idealized representation and the output thereof. In the multilayer networks 22', subsequently described all waveforms may be learned and the entire raw data or electrical signal input thereto and which converges and sorts the output to the different idealized waveforms.

As an alternative embodiment of the extraction network 22, the neural network 22 may learn a repetitive waveform and during the third pass extract any unique or substantially different waveform from the electrical signal and store that unique waveform in the buffer 30 for reducing 34. This would be an ideal application of EKG signals wherein unique signals other than the repetitive signal may be detected and subtracted by the network 22. The learned waveform may be input by the user, instead of learning. The network 22 then may use this templated waveform for the extraction. Either similar or dissimilar waveforms may be extracted.

Artificial Neural Network (ANNs) are highly parallel and distributed networks of interconnected simple processing elements. Such networks have potentially very powerful processing capabilities reminiscent of some of the human brain type processing capabilities like learning, associative memory, image recognition, generalization, and estimation. ANNs have been successfully applied in many difficult processing and computing applications like signal processing, image recognition, pattern classification, robot control, optimization, speech understanding and synthesis, expert system problem solving, and other difficult artificial intelligence applications.

Various ANN architectures have been proposed ranging from single-layer architectures of laterally interconnected processing elements ("neurons") to multiple-layer architectures with general interconnects. The basic ANN processing element can also vary in complexity from a simple processor, that performs a weighted-sum operation between a real valued input vector x and an internal computed weight vector W, to more powerful processors that attempt to simulate the functions of a brain cell.

The programming of a given ANN is accomplished by means of adjusting the interconnection weights (synapses) at each usually accomplished through a learning or a synthesis algorithm. Different learning algorithms are available for the training of single- and multiple-layer ANNs. Here, learning algorithms can be classified into two main classes: Supervised and unsupervised.

Supervised learning, or teacher assisted learning, in an ANN is characterized by the adaptation of the network interconnections and weights so that a set of input signals (vectors) are associated with a set of output "target" signals; i.e., the network is taught specific responses that correspond to specific inputs. This type of learning is mainly used in neural networks that are designed to operate as associative memories and is very useful in pattern recognition and classification applications. One learning mode for associative neural memory is autoassociative. In the autoassociative learning mode, the ANN is trained to respond with an exact replica of its input. The learning process leads to the formation of stable network states (memories), in a state space representation, which initial network inputs (initial states) and attracted to.

Unsupervised learning, on the other hand, allows the ANN to respond with its own outputs to a given set of inputs. In this learning mode, the network elements behave patterns (signals) in response to different input signals. The important thing to realize here is that the encoding of the network responses is unsupervised and is determined by the ANN architecture and its initial synaptic weights.

One particular ANN that is suitable for the identification of physiologic signals is the autoassociative neural memory (ANM) network 22. The network 22 consists of a fully interconnected single-layer of simple neurons whose transfer function is given by:

$$x = W.x \tag{1}$$

where x is a real valued n-dimensional vector representing the input signal and W is a real valued n×n matrix representing the network's synaptic weights. Equation (1) reflects the autoassociative processing mode of the network 22; it also models the association or retrieval process as a linear matrix/vector product operation. The recording of a given set of m n-dimensional training vectors (x) can be accomplished through the interconnection matrix W given by:

$$W = X.X+ \tag{2}$$

where X is an n x m matrix with x column vectors and X+ is the generalized inverse of matrix X (X+ =(Xt.X)−1.Xt if the vectors (x) are linearly independent). Equation (2) represents an optimal linear mapping in the sense of least-mean-square error. The learning rule of (2) requires to computational problems if the matrix Xt.X is an ill-conditioned matrix. An alternative dynamic learning rule that reduces the storage requirements, by considering the x vectors sequentially, W1 arbitrary $$Wk+1 = Wk + (a.k) - 1[xk.xkt - (Wk.xk).xkt]; \tag{3}$$

where k is the iteration number, xk is the kth training vector, t denotes transpose, and a can be selected as a constant or as an appropriate scalar function of vectors (x). Equation (3) converges to the optimum generalized inverse matrix W of (2) if the set (x) is cycled multiple times.

Such a network 22, has inherent high-performance characteristics like dynamic learning from partial samples, robustness, noise immunity, shift invariance, error correction, fault tolerance, and generalization. For example, once taught a given set of association patterns, the ANM 22' will be able to associate noisy and/or partial input patterns with the most "similar" learned pattern. Also, the ANM 22' performance is insensitive to input pattern distortion and/or synaptic weight variations sequential learning capabilities of ANMs can lead to "psuedounsupervised" learning or generalizations which is next shown to be very crucial in physiologic signal recognition and classification. The physical configuration of a neural network is commonly known in the art.

Figure 7:
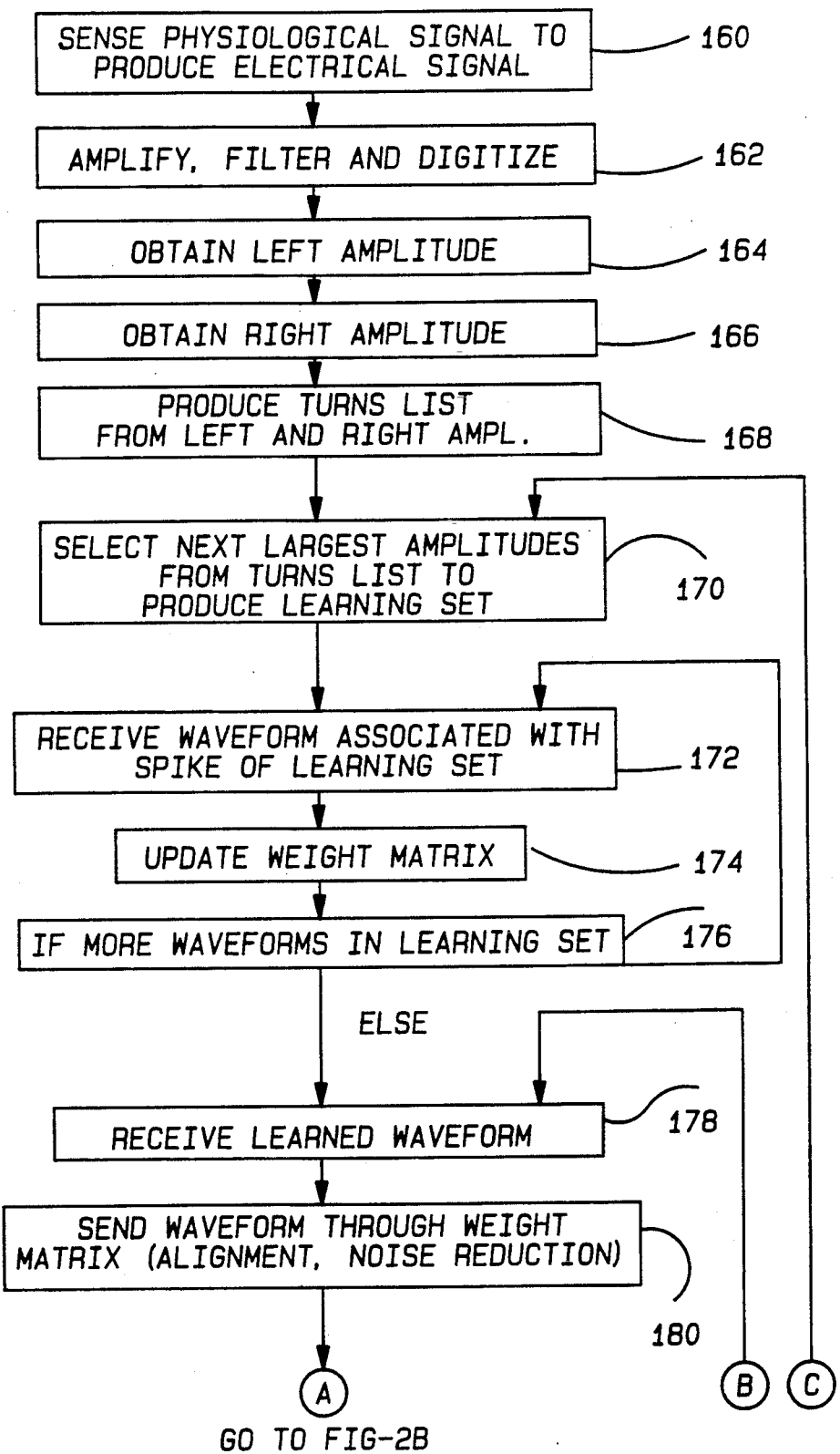
FIG. 7 is a flow chart defining a second embodiment of functions defining the block diagram of FIG. 1.

In the second embodiment as illustrated in the flowchart of FIG. 7, the control means 20 identifies and finds the peaks by an alternative method. The control means 20 develops a "turns list", comprising a table or an array of all peaks. The peaks are identified by measuring the amplitude of the left side and the amplitude of the right side formed about a peak or a turn. If both the left and the right amplitudes are greater than a predetermined number, a spike is identified. Furthermore, the slope of the peak must be less than a predetermined slope in order to be detected as a peak. Therefore, the turns list consists of an array which identifies the location of all the peaks which have satisfied the previous mentioned conditions. Steps 160, 162, 172–180 are similar to the steps of flowchart of FIGS. 2a-2b, whereas steps 164-170 add the new steps of the second embodiment of the control means 20.

After the turns list is developed, the learning means 24 develops a learning set. In the specific embodiment, the largest one hundred left amplitude and the largest one hundred right amplitudes are first assumed as by the number of peaks for one waveform. The union of the set of the largest one hundred left and the largest one hundred right amplitudes are taken, for example 30-50 waveforms will be obtained. From these waveforms, a learning set is developed which is assumed to comprise one waveform. To determine other waveforms, the second largest left and right amplitudes are considered, etc.

The weight matrix 26 learns the waveform. The waveform is learned as in the previous embodiment. Extraction means 28 then extracts the learned waveform. The extracting means 28 identifies the intersection sections of the left and right lists, which will be approximately 150 peaks. Each peak is then checked with the template. The original physiological input signal is input to the network 22 which compares the peaks to a template. A peak or waveform is excepted if the output is close to the template. All others are rejected. In general, 90 to 100 are accepted. In order to get the waveform, an average is taken of the accepted outputs. The waveform is then extracted from the link list or the turns list such that its peak will not be identified in subsequent passes.

Generally, network 22 as implemented, may receive an electrical signal or data and learn any repetitive waveform with the signal The same electrical signal is used for extracting a waveform based on the learned waveform In other words, an unknown is used for learning, and the unknown data are also used for the extracting. No preconceived waveform is necessary. The source of the electrical signal is irrelevant for the network 22 as long as there is a repetitive waveform.

Figure 8:
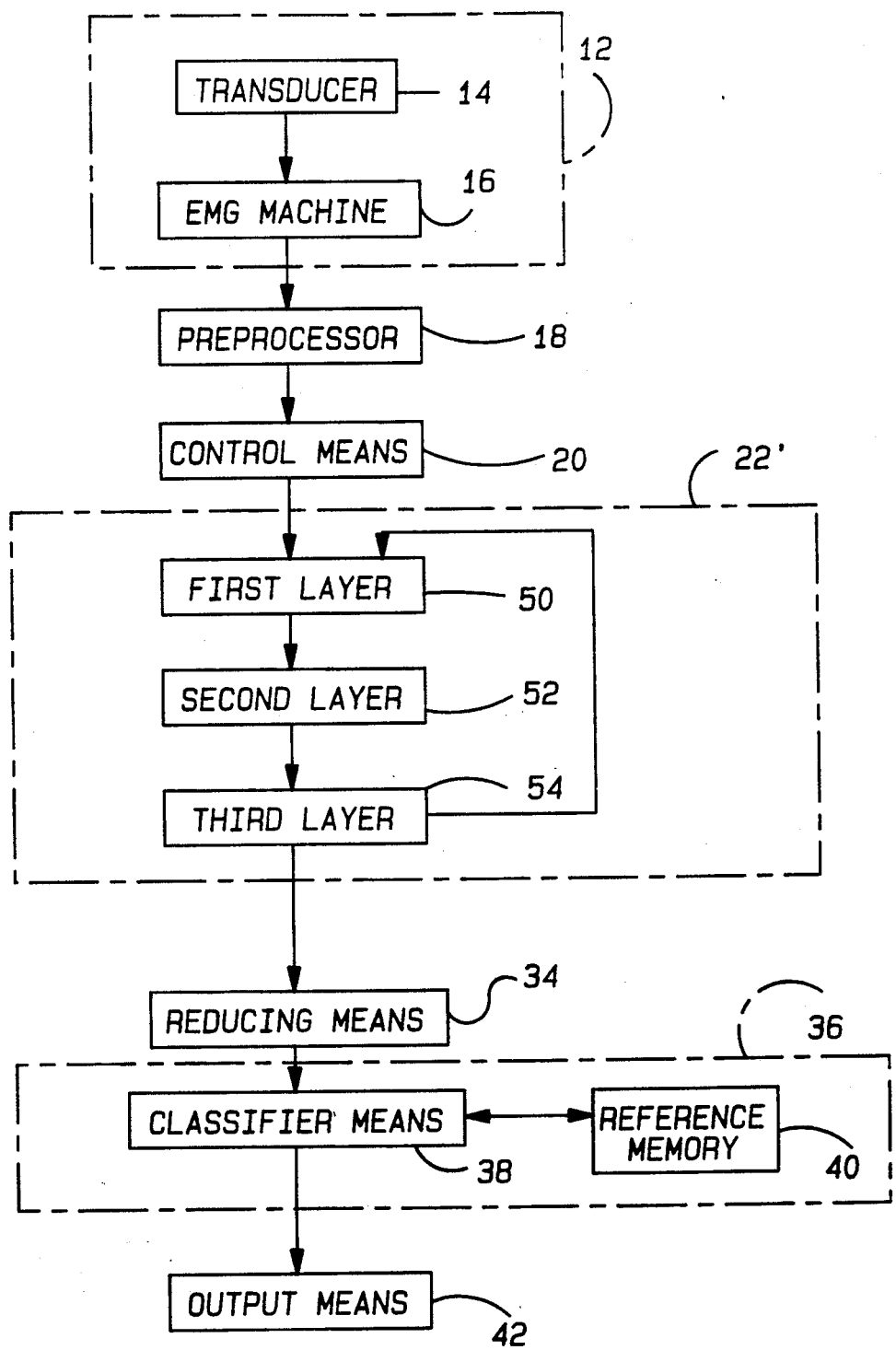
FIG. 8 is a block diagram of an alternative embodiment of the subject invention.
Figure 9A:
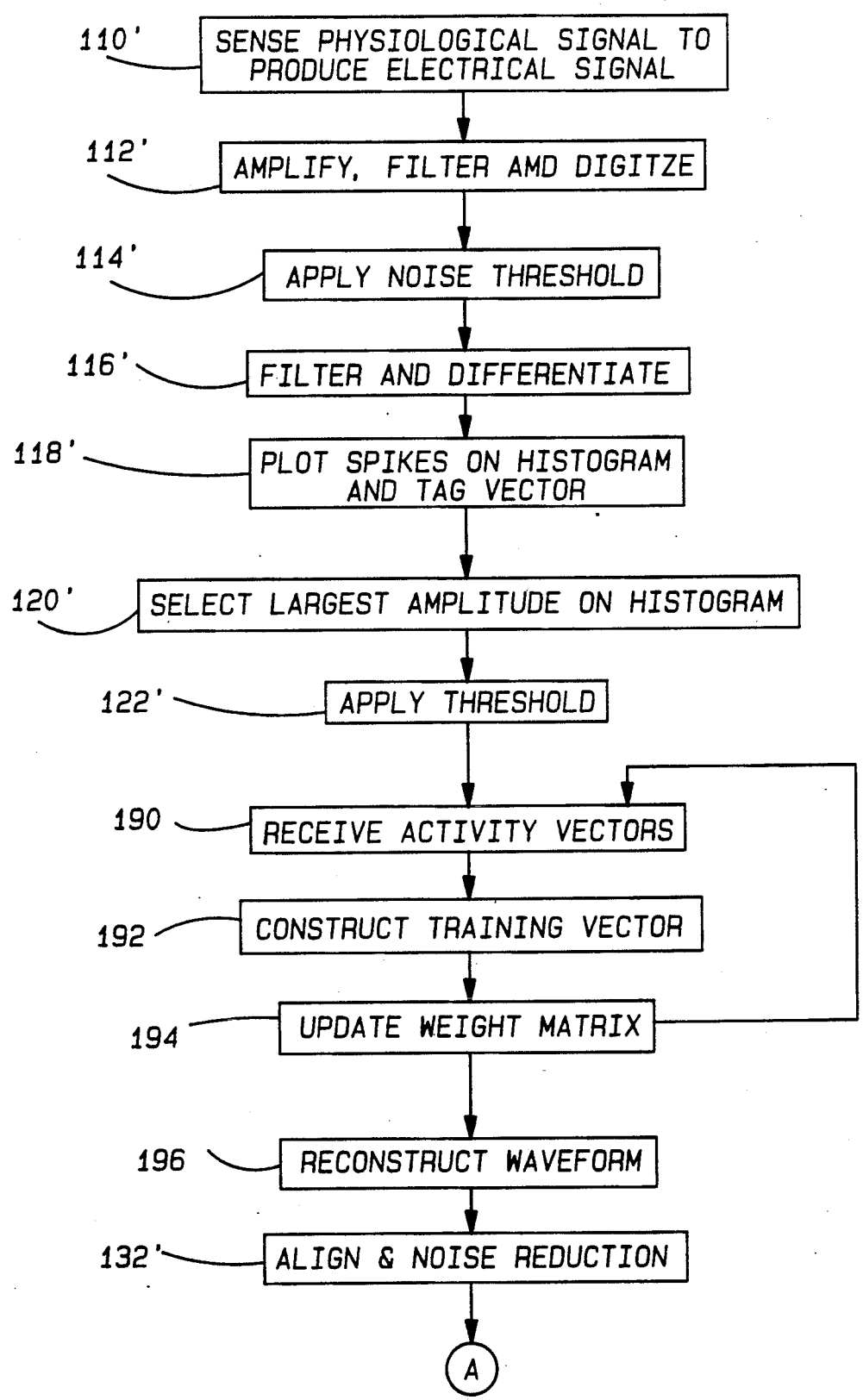
FIG. 9 is the flow chart defining the block diagram of FIG. 8.
Figure 9B:
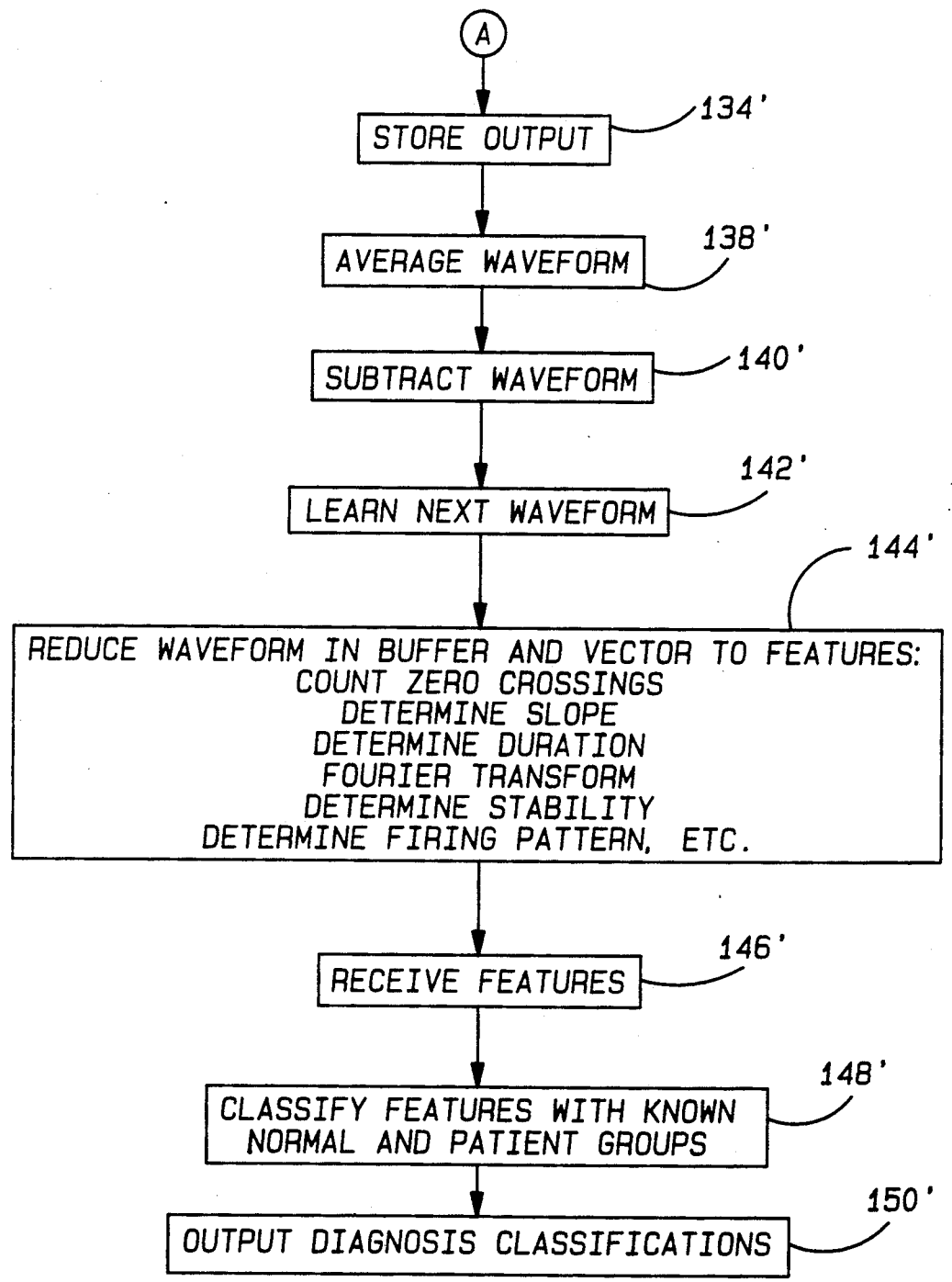

Alternatively, the neural network 22' may include a multilayer self organizing neural network such that a single pass of the electrical signal is only necessary in order to extract the waveform as illustrated in FIG. 8. As previously stated, the primary goal of the neural network 22' is the unsupervised recognition and decomposition of signals with superimposed repetitive pulses. The network 22' has no "a priori" knowledge of the shape or amplitude of the underlying signal pulses. The network 22' only assumes that all pulses to be learned have a pronounced peak, an estimated pulse duration upper bound, and a repetitive pulse pattern. Furthermore, the pulses are assumed to be asynchronous and nonperiodic. Finally, the diagnosed signal is assumed to be long enough so that a rich set of isolated and superimposed pulse waveforms is generated. Physiological signals, EMG, ECG, EEG, etc., and vehicle electronic sensor signals, and the presents of noise and undesired radiation coupling, are examples of the above signals. The flowchart of FIGS. 9a-9b illustrate the steps implemented by the means of FIG. 8. Primed numbers in FIGS. 9a-9b corresponding to unprimed numbers of FIGS. 2a-2b and represent like steps which are not further discussed.

The neural network 22' includes the following processing stages: locating potential pulse activities within the given signal, discovering the number of different pulses (classes) present and their underlying nominal shapes (a pulse may be distorted and/or noisy in addition to being superimposed with other pulses), and using the nominal pulse shapes as templates or library vectors in order to classify signal activity segments according to some error (or distance) measure. A three layer (two-hidden and one-output layers) self organizing neural network 22' that is capable of capturing, representing, classifying, and reconstructing noisy superimposed pulses is utilized. No initial pulse representations are assumed; the network 22' relies only on the repetitive nature of a set of unlabeled signal activities.

More specifically, sampled signal segments (activity vectors) of forty samples each are used as inputs to the three-layer network 22'. Activity vectors are selected such that signal peaks are aligned at the same position within the window of forty samples as illustrated in step 190. It is assumed that the signal duration covered by the forty activity vector samples represents an upper bound and all pulse durations present in the raw signal. An unlabeled training set consisting of all activity vectors with pronounced peaks is constructed in step 192. This is achieved by generating one forty-dimensional sample training vectors for each pronounced peak (peak amplitude exceeding 0.25), with the peak amplitude located at a fixed location within the training vector. Here, prior knowledge about the sharp positive peaks of the underlying pulses is used effectively and locating and aligning potential pulse occurrence; this in turn reduces the computational load for shift in variance that would otherwise constrain the learning in the neural network 22'. Steps 194, 196, 132'-142' illustrate the learning of the waveform. The first 50 and second 52 hidden layers of the neural network 22' have dimensions H and J, respectively, and employ neurons with signal activations operating over the activity interval. The output layer 54 has L=40 neurons with linear activations. The network 22' is applied in two phases; a learning/organizing phase and a retrieval phase. In the learning phase, activity vectors are presented one by one to the network (first inner acting with the H-dimensional hidden layer) and a self organizing learning strategy is used in order to capture the shapes of the underlying pulses. During this phase, the network 22' minimizes its available neurons at the two layers and forms a bottle neck at the second hidden layer (center layer) 52. The neural network 22' self-organizes such that the first layer 50 acts as a feature discover layer. The second hidden layer 52 acts as a encoder which generates efficient compact code (internal representation). Finally, during this phase, the output layer 54 is constrained in a way such that an approximate mapping between the internal presentation vectors and the sampled pulse space is realized; i.e., the output layer 54 is intended to reconstruct pulse or waveforms. In the retrieval phase, all learning is inhibited and the network 22' is used to map training activity-vectors as well as signal activity vectors not used during training, into their nominal superposition-filtered pulse waveforms. This is done by utilizing a dynamic architecture consisting of the trained three-layer net with a direct feedback connection from the output layer 54 to the first layer 50. An investigation of the dynamics of the retrieval network 22' reveals that stable internal representations lead to fast conversions to pulse/shape stage having wide base of attraction. This translates into having a network 22, that starts with a corrupted, usually due to superposition, activity vector as its initial state and, layer, dynamically converges to the closest pulse-shape state representing the underlying learned pulse waveform.

Figure 12:
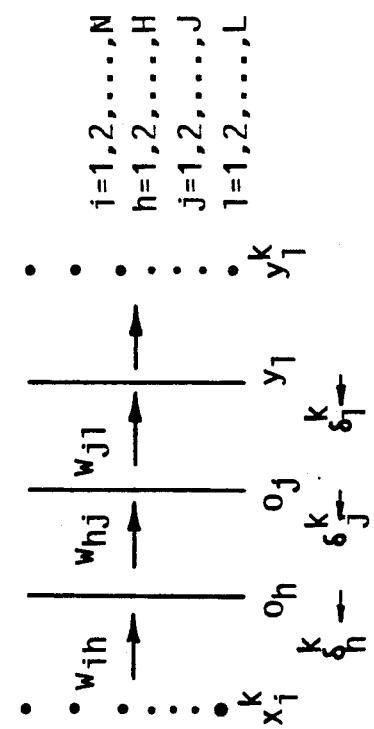
FIG. 12 is a three layer diagram for the alternative embodiment of FIG. 10.

A BEP-based self-organizing/generalizing training strategy is well suited for the problem at hand. First, the three-layer net signal/weight/error diagram is illustrated in FIG. 12. Here $x^k$ and $y^k = x^k$ represent the input and output activity vectors, respectively, 0 represents a layer's activation vector, and $\delta k$ is the familiar back-propagated error vector due to the $(x^k, y^k)$ training pair. The indices i, h, j, and l correspond to input, first hidden 50, second hidden 52, and output 54 signal components. The weights in all hidden units are updated according to the original BEP algorithm (with no momentum term): first hidden layer 50: $\Delta w_{ih} = P\delta_h x_i$ and second hidden layer: $\Delta w_{hj} = p\delta_j O_h$ where $p = p$. $(pm)^k$, $O < p. < 1, pm$ very close to but less than 1, and k is the training pattern number. The local update rule for the output layer 54 weights is given by:

$$\Delta w_{ji} = p\delta_j O_j + \beta p w_{ji} \text{ with } \beta < p.$$

From the above weight update equations, it is seen that two modifications to the BEP algorithm have been incorporated: exponentially damped learning coefficients and output layer "forgetting" effects. The damping in the learning coefficient is very crucial in balancing learning against the emphasis of last-learned patterns (which could, in our problem, be undesired highly-superimposed activity vectors). It also has the added advantages of learning "annealing" and allowing an initially relatively large learning coefficient to be used which accelerates the learning process. On other the hand, the forgetting effects at the output layer 54 are very important in enhancing the learning of repetitive structured patterns as opposed to superimposed patterns and/or noise. This latter strategy also helps in realizing a more accurate mapping (reconstruction of pulse-shape patterns) between the second hidden layer 52 and the output layer 52. It also has desirable effects on the generalization and self-organization of the hidden layers, indirectly through the propagation of more accurate $\delta$s from the output layer 54.

A strategy for hidden unit elimination is based on back-propagated error magnitude distributions. This strategy allows for the elimination of undesired hidden units according to their history of error generation. The strategy also allows for unit elimination in networks with multiple hidden layers. More specifically, it allows for selective hidden layer reduction based on a prior knowledge of the hidden layer functionality; e.g., in our problem we employ the proposed unit elimination strategy such that both hidden layers are optimized with the first layer 50 being less constrained than the second layer 52, which leads to a gradual bottleneck in realizing feature extraction/encoder combinations layers. The following is the strategy we have employed for hidden layer size minimization.

1. Divide the training set into groups of K vectors each, with K being a small fraction of the training set m.

2. Use BEP algorithm as modified above and train the net with the first set of K sample Set $K_o$ to K.

3. Holding all network weights fixed, compute the accumulated error signals for all hidden neurons:

$$e_j = \sum_{K=K_o}^{K+k_o} (\delta_j^K)^2;$$

j=1, 2, ..., j for second hidden layer neurons and $$e_h = \sum_{K=K_o}^{K+k_o} (\delta_h^K)^2;$$

h=2, 2, ..., H for first hidden layer neurons

4. Compute the means and standard deviations for accumulated error signals:

$(\mu_j, \sigma_j)$ for 2nd hidden layer and $(\mu_H, \sigma_H)$ for 1st hidden layer 5. One neuron j (from 2nd hidden layer) is deleted iff $e_j > \mu_j + 1.4\sigma_j$ and $e_j > e_{i \neq j}$ for all i.

6. One neuron h (from 1st hidden layer) is deleted iff $e_h > \mu_H + 1.8\sigma_H$ and $e_h > e_{i \neq h}$ for all i and no deletions are made in step 5.

7. After deletions, update the network weights by learning the present set of K patterns using the proposed learning algorithm. Set $K_o = k_o + K$. Stop if the limit on the number of training cycles is met, if not, Go to step 2.

The first thing to note about the above redundent-hidden-unit elimination algorithm is the utilization of the accumulated back-propagated decision error signal over a sample subset of the training set. This differs from earlier-proposed penalty criteria for hidden-unit elimination. Here, a hidden unit is eliminated based 1) on a short history of its contribution to the output mapping inconsistencies and 2) on its behavior compared to all other units in a given hidden layer. Due to the nature of the training activity vectors, the choice of K in step 1 above is flexible. The larger K is the value of the accumulated error e in step 3. (One extreme is to choose K=m, the number of training vectors. However, this might not be possible in situations where only a fraction of the training vectors are available at a time.) The unit elimination recipe is then given in steps 5 and 6. Here, one unit in a given hidden layer is eliminated, after each K-vector presentation, if it has the largest accumulated decision error e in that layer and if e exceeds a threshold determined by the distribution (mean and standard deviation) of all units' accumulated decision errors in that layer and a preset vigilance parameter (the 1.4 value used in the inequality of step 4). The above algorithm is also capable of realizing a gradual bottleneck when more than one hidden layer is used. This is accomplished according to step 6 above, where unit deletions may only be performed if no such deletions occur in the next higher level hidden layer. Another factor effecting the size of lower-level hidden layers is the magnitude of the associated vigilance parameter (set to 1.8 for the first hidden layer in our simulations). The vigilance value is set larger than that of the next higher-level hidden layer as seen in steps 5 and 6 above. This strategy allows the network to establish the desired cascade of a constrained feature extraction layer followed by a more constrained encoder layer/bottleneck.

Figure 10:
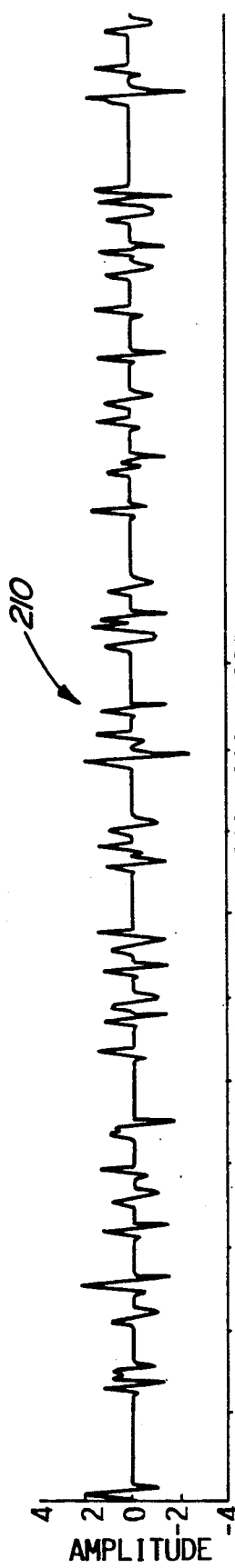
FIG. 10 is an electrical signal used in an example of the alternative embodiment.
Figure 11:
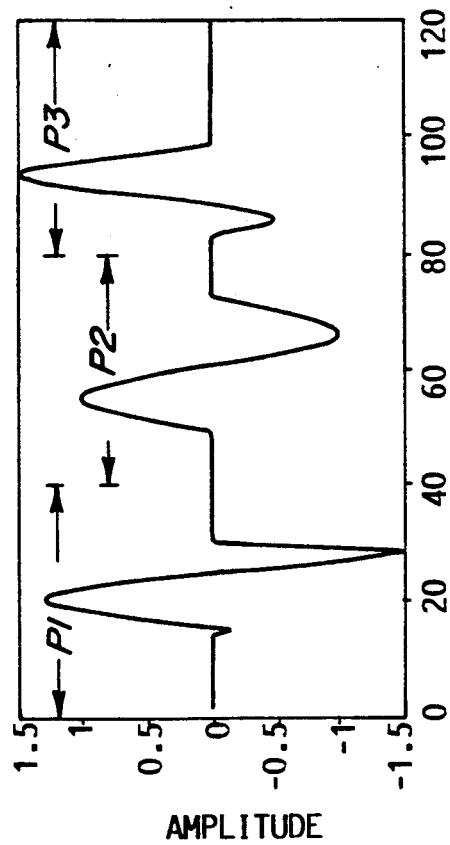
FIG. 11 are the waveforms of the signal of FIG. 10.

The performance of the above dynamic multiple-layer neural network 22' and its proposed self-organizing training algorithm is evaluated using simulated signals of superimposed repetitive pulses of various degrees of complexity. An example of the decomposition of one particular signal is shown at 200 in FIG. 10. The signal in FIG. 10 represents the first segment of 1800-time units of a simulated 8000 time unit signal. This signal is constructed as the superposition of three pulse trains. Each pulse train is constructed from one fixed pulse waveform that repeats with a restricted random frequency. The three pulse waveforms used are labeled p1, p2, and p3 and are shown in FIG. 11. The overall superimposed signal referred to as the raw signal of FIG. 10 has a total of 192 pronounced signal peaks which are used to locate and align the activity-vectors as previously explained. An unlabeled training set of 192 activity-vectors is used in the following simulations. Visual inspection of the training set reveals the presence of 68 clean (nonsuperimposed) pulse waveforms: twenty-four, twenty-two, and nineteen waveforms belonging to p1, p2, and p3, respectively. Therefore, the training set has about 64% distorted (superimposed) pulse waveforms, each involving two or three pulses. It is to be noted here that the visual identification of 68 clean pulses is made easy because of out prior knowledge of the shapes of the underlying pulses; this prior knowledge is not made available to the network. The network is supposed to discover these underlying pulse waveforms as part of its learning phase.

The network 22' described previously is used. This initially had six neurons in the first and second hidden layers, respectively. An input window size of forty ($+1$ for bias) is used, with the leftmost activity-vector peak centered as the thirteenth input bit. The output layer has forty neurons with linear activations (slope=1). Only feed-next connections are allowed during the learning phase, with biases of $-1$ applied to all units. Initially, all weights are set randomly in the interval $[+.1, -.1]$. The BEP-based learning algorithm is used for training the network. The following parameters were used: learning coefficient $p=0.35(0.995)^k$, number of learning cycles=5 (a total of 192*5=960 presentations), K =30 (i.e., 192/30=6 training vector subgroups), and output layer weight decay factor B=0.05.

During the first cycle in the learning phase, the network 22' eliminated three units from the second hidden layer 52, and thus reduced its neurons to three. In the second learning cycle, only one unit was eliminated from the first hidden layer 50. The learning proceeded from the second cycle to the fifth with no further hidden unit elimination. Learning stopped after the fifth cycle and the trained network was used in the dynamic retrieval phase as previously described. Here, all 192 training activity vectors are tested and mapped by the trained network into "closest" underlying representations. In this simulation, the network 22' has discovered four internal representations; three representations corresponded to the three underlying pulses, respectively, and one representation corresponded to a falsely identified pulse. In terms of network dynamics, each representation is manifested as a strong stable point in the $R^{40}$ dimensional state-space. We were very impressed by the stability and speed of convergence of the retrieval network 22'. The above simulation was repeated over thirty times, each time with new weight initialization and/or different learning parameters and K values (e.g., $P_0=0.15, 0.3, 0.4$; K=30, 40, 50). In most cases, the network 22' discovered the five-three hidden layer arrangement and led to network dynamics comparable to the above. In some cases, the network learned two out of three representations (two pulse representations were merged into one) and one or two additional false representations (attractors) which attracted less than 10% of the activity-vectors. The network 22' was also able to generalize and form meaningful internal representations when initialized between five and ten neurons/hidden layer. In all cases, five learning cycles seemed to be sufficient.

The assembly 10 includes reducing means 34 for analyzing the waveforms stored in the neural network 22, 22' or in the buffers 30 to produce features separately characterizing each waveform. Once the motor unit waveforms are obtained, there is a standard procedure to the reduction of the information into tabulated features. Such a procedure includes looking at zero crossings, the slope, duration and amplitude, etc. The reducing means 34 is implemented through software. The reducing means 34 will look at each waveform in the buffers 30 and the time table, along with the original sampled electrical signal. Examples of features obtained are mean duration, histograms of duration, amplitude, number of turns of the waveform, Fourier transform—median frequency or high and low frequency contents ratio, stability of waveform (compared with every occurrence in original data—extract variation), firing pattern (regular or irregular—and relation to amount of muscle force using and number of MUs used). This list is not exhaustive, and the more features used in characterizing the waveform, the better the classification, as subsequently described.

The assembly 10 includes classifier network means 36. The classifier network means 36 includes reference memory means 40 for containing information comprising features and combinations thereof associated with disease states for comparing the features to the information to produce an output representative of diseased states based on the best match of the features with the information. The classifier network means 36 comprises a different neural network processor. The features from the reducing means 34 are fed into the classifier neural network 36 and the features of the waveforms are compared to the information representing normal and patient groups characteristic features which represents the normal and disease states. This normal and patient groups information is stored in the reference memory means 40 of the classifier neural network 36 in weight matrix form and is characterized by the same type of features as those characterizing the motor unit waveforms from the reducing means 34. The features of the motor unit waveforms are compared to this information and the best matches are noted. All the features are considered in determining the pattern of features and an output is given to categorize them. The classifier neural network 36 takes the total number of features and classifies them giving the best match. Wrong or deviant features may be ignored in obtaining the best category In other words, the neural network 36 performs a state space transformation from a feature vector space to a diagnostic classification space. The features go through nonlinear mapping which accomplishes the transformation. The neural network 36 acts as a result of the learning of disease states by learning features and combinations thereof representative of particular disease states from patient groups. The network 36 is an adaptable network with trained diagnosis. The network 36 is trained in the same manner as network 22 by updating the weight matrix based on new features associated with a diagnosis. The information of how to accomplish the transformation is stored in the neural network 36 in a distributed manner. No one point or connection in the neural network 36 contains only one piece of information, but the combination of various points and connections provide the information. The architecture of neural networks is commonly known in the art.

The classifier neural network 36 includes an output means 42 for outputting physiologic information to aid the physician in diagnosing the disease. The physiologic output categories or classification may include disease output such as muscle disease, upper motor neuron disease, axonal neuropathy, neuro muscular junction disease, etc. The neural network 36 will output percentage ratings to the different physiologic diseases from 0% to 100% such that the physician will be informed of multiple symptoms and the proportional percentage of likelihood. In addition to the physiologic outputs, the original electrical signal and extracted motor units are printed out for consideration by the physician. The output means 42 may include a printer or graphic device for printing out hard copies of all the information recited above.

The invention includes a method of discriminating physiological electrical signals produced within the body and producing output indicative of disease characteristics. The method includes the steps of sensing 110, 110' the electrical signals produced within the body, applying a noise threshold 114, 114', filtering and differentiating 116, 116' the electrical signal to isolate spikes associated with occurrences of the repetitive waveform, identifying spikes and plotting the histogram 118, 118', applying the trough threshold to identify spikes, associated with a single motor unit 120-122, 120'-122', learning 124-138, 190-196 and 132-13 a repetitive waveform within the electrical signal by updating the weight matrix, extracting 140, 140' the learned waveform from the electrical signal, storing 134, 134' the extracted waveform and averaging the waveforms associated with a singles motor unit and storing associated times of occurrence of the waveform within the electrical signal, subtracting the extracted waveform from the electrical signal, reducing 144, 144' the waveform into features characterizing the waveform, analyzing 146-150, 146'-150' the features with respect to information comprising standard features and combinations thereof associated with disease states, and outputting 42 diseased states data based on the best match of the features with the information.

Figure 5:
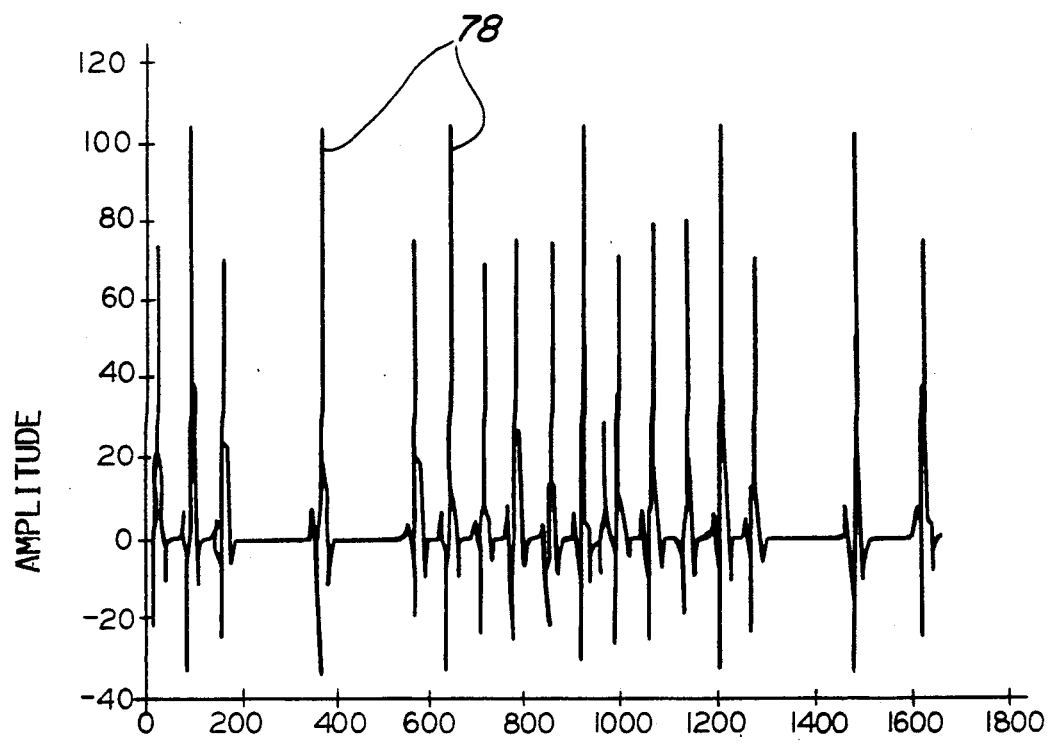
FIG. 5 illustrates reconstruction of a motor unit.

FIGS. 3 through 6 illustrate the effects of the subject invention as applied to an electrical signal. FIG. 3 illustrates a simulated EMG signal comprised of two motor units with regular firing rates superimposed and with noise added. The EMG signal is detected by the sensing means 12 and then sent through the preprocessing means 18 for filtering and differentiation. A histogram will be made by the extraction network means 22, and a first motor unit grouping selected representing the greatest amplitude grouping. The motor unit is learned. FIG. 4 indicates the learned motor unit waveform 72 (solid line), and a misaligned, noisy occurrence 74 (large dashes) presented to the extraction network 22, and the output 76 (dotted line) is aligned and noise is rejected. FIG. 5 indicates reconstruction of one motor unit 78 by the extraction network 22. Firing information may then easily be derived and the missing occurrences checked (gaps on time line). The output in FIG. 5 may be printed out for the physicians review, but otherwise the information is stored in the timetable and buffer 30. FIG. 6 indicates the electrical signal 80 after the first motor unit is subtracted. The remaining peaks correspond to the second motor unit. The process is then repeated to learn and extract the second motor unit. The learned waveform of FIG. 4 is the waveform stored in the buffer 30 for the first motor unit, which is then reduced by the reducing means 34.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims wherein reference numerals are merely for convenience and are not to be in any way limiting, the invention may be practiced otherwise than as specifically described.

What is claimed is:

1. A wave analysis assembly for discriminating electrical signals and for producing output indicative of disease characteristics, said assembly comprising; means (12) for producing an electrical signal, control means (20) for identifying the location of individual unknown waveforms occurring about a peak within said electrical signal and producing a set comprised of the individual unknown waveforms, extraction neural network (22, 22') having a distributed network of synaptic weights for receiving said set and for learning the unknown waveform within said electrical signal through a mapping transformation of said individual waveforms of the set in the distributed network of synaptic weights to develop and store an idealized representation of the unknown waveform producing a learned waveform and for extracting said learned waveform from said electrical signal, and output means (42) for outputting information based on said extracted waveform.

2. An assembly as set forth in claim 1 further characterized by said network (22, 22') including weight matrix means for storing an idealized representation of the repetitive waveform by synaptic weights and updating the synaptic weights by an error signal.

3. An assembly as set forth in claim 2 further characterized by said neural network (22, 22') including learning means for receiving one of said unknown waveforms and an output waveform produced by sensing said unknown waveform through said weight matrix, and comparing said unknown waveform and said output waveform to produce said error signal.

4. An assembly as set forth in claim 3 further characterized by said neural network (22') comprising a multilayer network for receiving the learning sets of all waveforms and for learning and extracting the waveform in a first pass over the electrical signal.

5. An assembly as set forth in claim 1 further characterized by including reducing means (34) for analyzing said extracted waveform to produce features characterizing said waveform.

6. An assembly as set forth in claim 5 further characterized by including classifier network means (36) containing standard features and combinations thereof associated with states for comparing said features to said standard features and combination to produce an output representative of states based on the best match of said features with said information.

7. An assembly as set forth in claim 6 further characterized by said extraction network means (22, 22') including buffer means for storing said extracted waveform of said electrical signal.

8. An assembly as set forth in claim 7 further characterized by said extraction network means (22, 22') including learning means for learning said repetitive waveform and a weight matrix means (26) for storing said learned waveform.

9. An assembly as set forth in claim 8 further characterized by said extraction network means (22) including subtracting means (32) for subtracting said learned waveform from said electrical signal.

10. An assembly as set forth in claim 9 further characterized by said neural network (22) comprising a single layer network for receiving one learning set for a waveform and learning the waveform in a first pass and extracting the waveform in a second pass over the electrical signal.

11. A wave analysis assembly for discriminating physiological signals produced within the body and for producing output indicative of disease characteristics, said assembly comprising; means for supplying a plurality of independent features characteristic of a waveform contained within a physiological signal, a classifier neural network (36) having a nonlinear distributed network of learned features and combinations thereof associated with a plurality of disease and normal patient states for transforming the features characterizing the physiological signal through the distributed network to produce an output representative of any of said plurality diseased and normal states, and output means for receiving the output and indicating the diseased and normal states.

12. An assembly as set forth in claim 11 further characterized by said classifier neural network (36) including reference memory means (40) comprised of a weight matrix for storing the learned features and combinations for diagnosis and for nonlinearly mapping said features within said weight matrix to produce said output.

13. An assembly as set forth in claim 12 further characterized by including sensing means (12) for sampling a physiological signal produced within the body and for producing an electrical signal.

14. An assembly as set forth in claim 13 further characterized by including reducing means (36) for analyzing said electrical signal and for producing features characterizing said electrical signal.

15. An assembly as set forth in claim 14 further characterized by including extraction network means (22, 22') for receiving said electrical signal and identifying and learning a waveform comprising said electrical signal and for extracting said learned waveform, and for storing said extracted waveform and associated times of occurrence of substantially similar waveforms within said electrical signal.

16. An assembly as set forth in claim 15 further characterized by including preprocessing means (18) for filtering and differentiating said electrical signal to isolate spikes associated with waveforms.

17. An assembly as set forth in claim 16 further characterized by including control means (20) for controlling said extraction network means (22) and for identifying waveforms in said electrical signal.

18. A wave analysis assembly for discriminating electrical signals having a waveform, said assembly comprising; input means (12) for sampling an electrical signal, control means (20) for identifying the location of individual unknown waveforms occurring about a peak within said electrical signal and producing a set comprised of the individual unknown waveforms, extraction neural network (22, 22') having a distributed network of synaptic weights for receiving the set and for learning the unknown waveform by a mapping transformation of said individual waveforms of the set in the distributed network of synaptic weights to produce a learned waveform and for extracting the learned waveform from the electrical signal, and output means (42) for outputting information of said extracted waveform, said extraction neural network including learning means for learning a template waveform inputted by the user for the extraction.

19. An assembly as set forth in claim 18 further characterized by said extraction neural network (16) including extracting means (28) for extracting waveforms from said electrical signal substantially similar to said learned waveform.

20. A method of discriminating electrical signals and producing an output, said method comprising the steps of: sensing the signals and producing an electrical signal, identifying the location of individual unknown waveforms occurring about a peak within the electrical signal, producing a set comprised of the individual unknown waveforms, learning the unknown waveform within the electrical signal by a mapping transformation of the individual waveforms of the set in a distributed network of synaptic weights to produce a learned waveform, extracting the learned waveform from the electrical signal, and outputting information based on the extracted waveform.

21. A method as set forth in claim 20 further characterized by storing an idealized representation of the repetitive waveform by synaptic weights.

22. A method as set forth in claim 21 further characterized by receiving an unknown waveform and sending same through the weights to produce an output waveform.

23. A method as set forth in claim 22 further characterized by comparing the unknown waveform to the output waveform to produce an error signal.

24. A method as set forth in claim 23 further characterized by updating the synaptic weights by the error signal.

25. A method as set forth in claim 24 further including filtering and differentiating the electrical signal to isolate spikes associated with occurrences of the repetitive waveform.

26. A method as set forth in claim 25 further including reducing the waveform into features characterizing the waveform.

27. A method as set forth in claim 26 further including analyzing the features with respect to information comprising standard features and combinations thereof associated with disease states.

28. A method as set forth in claim 27 further including outputting states data based on the best match of the features with the information.

29. A method as set forth in claim 28 further including storing the extracted waveform and associated times of occurrence of the waveform within the electrical signal.

30. A method as set forth in claim 29 further including subtracting the learned waveform from the electrical signal.

31. A method for discriminating physiological signals produced within the body and for producing output indicative of disease characteristics, the method including the steps of; producing a plurality of independent features characteristic of a waveform contained within a physiological signal, learning and storing known features and combinations thereof associated with a plurality of disease and normal patient states in a distributed network, transforming the features through the distributed network to produce an output signal representative of any of said plurality of diseased states.

32. A method as set forth in claim 31 further characterized by storing the known features and combinations thereof in a weight matrix, and nonlinearly mapping the features within the weight matrix to produce the output.

33. A method as set forth in claim 32 further characterized by acquiring additional features and combinations thereof associated with disease and normal patient states, and training the distributed network by updating the weight matrix with the additional features and combinations thereof associated with disease and normal patient states.

* * * * *